United States Patent
De Rosa et al.

(10) Patent No.: US 10,266,611 B2
(45) Date of Patent: Apr. 23, 2019

(54) HYBRID COOPERATIVE COMPLEXES OF HYALURONIC ACID

(71) Applicant: ALTERGON S.A., Lugano (CH)

(72) Inventors: Mario De Rosa, Naples (IT); Antonella D'Agostino, Marano (IT); Annalisa La Gatta, Quarto (IT); Chiara Schiraldi, Naples (IT)

(73) Assignee: ALTERGON S.A., Lugano (CH)

( * ) Notice: Subject to any disclaimer, the term of this patent is extended or adjusted under 35 U.S.C. 154(b) by 236 days.

(21) Appl. No.: 14/974,657

(22) Filed: Dec. 18, 2015

(65) Prior Publication Data

US 2016/0102154 A1    Apr. 14, 2016

Related U.S. Application Data

(63) Continuation of application No. 13/820,838, filed as application No. PCT/EP2011/065633 on Sep. 9, 2011, now abandoned.

(30) Foreign Application Priority Data

Sep. 9, 2010    (IT) .............. MI2010A1635

(51) Int. Cl.
| | | |
|---|---|---|
| *C08L 3/02* | (2006.01) | |
| *C08L 5/02* | (2006.01) | |
| *C08L 5/08* | (2006.01) | |
| *C08L 5/16* | (2006.01) | |
| *C08B 37/00* | (2006.01) | |
| *C08B 37/02* | (2006.01) | |
| *C08B 37/08* | (2006.01) | |
| *C08B 37/16* | (2006.01) | |
| *A61K 31/715* | (2006.01) | |
| *A61K 31/728* | (2006.01) | |
| *A61K 31/737* | (2006.01) | |

(52) U.S. Cl.
CPC ........ *C08B 37/0072* (2013.01); *A61K 31/715* (2013.01); *A61K 31/728* (2013.01); *A61K 31/737* (2013.01); *C08B 37/0009* (2013.01); *C08B 37/0012* (2013.01); *C08B 37/0021* (2013.01); *C08B 37/0069* (2013.01); *C08L 3/02* (2013.01); *C08L 5/02* (2013.01); *C08L 5/08* (2013.01); *C08L 5/16* (2013.01)

(58) Field of Classification Search
CPC .. A61K 9/0048; A61K 9/0051; A61K 31/715; A61K 31/726; A61K 31/728; A61K 31/718; A61K 31/721; A61K 31/724; C08B 37/0063; C08B 37/0069; C08B 37/0072; C08B 37/0012; C08B 37/0021; C08L 3/02; C08L 5/00; C08L 5/02; C08L 5/08; C08L 5/16

See application file for complete search history.

(56) References Cited

U.S. PATENT DOCUMENTS

| | | |
|---|---|---|
| 4,920,104 A | 4/1990 | DeVore et al. |
| 5,442,053 A | 8/1995 | Valle et al. |
| 6,891,035 B2 | 5/2005 | Ljungquist |
| 2005/0250737 A1* | 11/2005 | Hughes ................ A61K 9/0048 514/58 |
| 2006/0194758 A1 | 8/2006 | Lebreton |
| 2007/0010481 A1 | 1/2007 | Balazs et al. |
| 2007/0059276 A1 | 3/2007 | Bergman et al. |
| 2007/0141101 A1 | 6/2007 | Nugent et al. |
| 2009/0163441 A1 | 6/2009 | Gobbo et al. |
| 2010/0098794 A1 | 4/2010 | Armand |
| 2010/0184720 A1* | 7/2010 | Gavard Molliard ........ A61K 9/0024 514/54 |
| 2010/0226988 A1 | 9/2010 | Lebreton |
| 2011/0071106 A1* | 3/2011 | Pizzoni ................ A61K 31/716 514/54 |
| 2011/0201571 A1* | 8/2011 | Gavard Molliard ........ A61K 9/0024 514/54 |

FOREIGN PATENT DOCUMENTS

WO    WO20100524430    *    5/2010

OTHER PUBLICATIONS

Boca, B. et al "An overview of the validation approach for moist heat sterilization . . . " Pharm. Technol., pp. 62-70. (Year: 2002).*
Berriaud, et al, "Rheological study on mixtures of different molelcular . . . ", Int. J. Biol. Macromol., vol. 16 1994.
Gomis, et al., "Effects of different molecular weight elastoviscous . . . " Arthritis & Rheumatism (2004) vol. 50, No. 1, pp. 314-326.
Karlsson, et al. "Determination of the distribution of molecular masses of sodium . . . " Journal of Chromatography A, vol. 986, pp. 67-72, 2003.
Lowry, et al., "Thermal Stability of sodium hyaluronate in aqueous solution," Journal of Biomedical Materials Research, vol. 28, pp. 1239-1244, 1994.
Nishimura, et al., "Role of chondroitin sulfate-hyaluronan . . . " Biochimica and Biophisica Acta, vol. 1380, pp. 1-9, 1998.
International Search Report of PCT/EP2011/065633 dated Jul. 12, 2012.

* cited by examiner

*Primary Examiner* — Leigh C Maier
(74) *Attorney, Agent, or Firm* — Silvia Salvadori, P.C.; Silvia Salvadori

(57) ABSTRACT

Describes cooperative hybrid complexes of hyaluronic acid, a simple and economical method for production thereof and use thereof in the area of medicine, cosmetics and food.

12 Claims, No Drawings

HYBRID COOPERATIVE COMPLEXES OF HYALURONIC ACID

This application is a continuation application of U.S. Ser. No. 13/820,838 filed on Mar. 5, 2013, which is a U.S. national stage of PCT/EP2011/065633 filed on Sep. 9, 2011, which claims priority to and the benefit of Italian Application No. MI2010A001635, filed on Sep. 9, 2010, the contents of which are incorporated herein by reference in their entireties.

FIELD OF THE INVENTION

The present invention relates to the field of products based on hyaluronic acid.

PRIOR ART

Hyaluronic acid, generally indicated hereinafter, together with its salts, called hyaluronans, as HA, is a negatively charged straight-chain polysaccharide, made up of a repetition of n disaccharide units (–4GlcUAβ1-3GlcNAcβ1-), in which D-glucuronic acid (GlcUA) and N-acetyl-D-glucosamine (GlcNAc) are joined with alternating β-1,3 and β-1,4 glycosidic bonds.

HA is a highly water-soluble polysaccharide and solutions of HA display a non-Newtonian type of viscoelastic behaviour. These properties depend on the molecular weight (and therefore, as HA is a linear polymer, on the length of the chain), the concentration, the pH and the ionic strength.

Owing to its biological properties and functions, HA has high added value (its commercial value greatly exceeds that of the other natural polysaccharides), with applications that range from the medical sector to cosmeceuticals and nutraceuticals. Its viscoelastic properties, coupled with the complete absence of toxicity or immunogenicity (the structure of HA is always the same in all living organisms in which it is present), have led to varied and extensive applications.

In many of these applications the performance depends on the molecular weight of the HA. For this, the average molecular weight of HA and the polydispersity index Mw/Mn (which measures the width of the curve of molecular weight distribution, where Mn is the number-average molecular weight, defined as the total weight of all the polymer molecules in a sample divided by the total number of molecules, and Mw is the weight-average molecular weight, which takes into account the varying mass of the molecules present) must be the gold standards to be considered when developing production processes for HA and strategies for application.

In particular, the wide variety of biological responses of HA connected with its molecular weight now mean that low molecular weight HA (L-HA) and high molecular weight HA (H-HA) must be used in context.

DESCRIPTION OF THE INVENTION

The present invention describes cooperative hybrid complexes between L-HA and H-HA, designated with the acronym L/H-HA, their characteristics, the production process thereof and use thereof in the area of medicine, cosmetics and foodstuffs. Weak forces, such as hydrogen bonds or hydrophobic interactions, can give rise to very stable interactions between molecules, if these are of the cooperative type. Cooperativity develops when it is possible for multiple bonds to form between the molecules, and being weak, they break randomly thereafter, but can immediately reform owing to the existence of intact vicinal bonds, which maintain the structural components of the bond at a distance useful for its reformation.

The molecules of HA in solution are characterized by cooperative phenomena of interaction based on formation of hydrophobic bonds and interchain hydrogen bonds, and the cooperativeness of these interactions depends on the length and therefore on the molecular weight of the chains. The long chains of H-HA give stable interactions between them, which involve all the molecules present in solution, giving rise to a three-dimensional network, whereas molecules of L-HA give interactions that are less stable, leading to systems of aggregation that do not simultaneously involve all the molecules present, which instead interact in clusters. This differing mode of aggregation of H-HA and L-HA in solution is responsible for the large differences in rheological behaviour, such as for example the viscosity of solutions of HA, which is a very important property for numerous applications, especially in the medical field.

The rapid drop in viscosity of solutions of HA as a function of the molecular weight in fact actually depends on this varying capacity for intermolecular interaction, so that, at equal concentration, solutions of H-HA with molecular weight above $1 \cdot 10^6$ Da have viscosities of higher orders of magnitude than those of solutions of L-HA with molecular weight between $5 \cdot 10^3$ and $5 \cdot 10^5$ Da. Owing to the strong cooperativeness of the interactions between the long chains of H-HA, when L-HA is dissolved in a viscous solution of H-HA, in the short term no significant differences in viscosity of the resultant solution are observed, indicating that the two molecular populations behave independently and that the formation of L/H-HA cooperative hybrid aggregates is a thermodynamically unfavourable process. Only with the passage of time (days-weeks), a slow but constant decrease in viscosity is observed that cannot be attributed to hydrolytic processes, and this effect is more evident if the molecular weight of the L-HA is less than $10^5$ Da. The continual variation of the physicochemical properties, in particular the viscosity, of these solutions makes them unsuitable for practical applications, which instead require constant rheological characteristics.

It is therefore clear, in view of the foregoing, that cooperative hybrid complexes between hyaluronic acid of low molecular weight and hyaluronic acid of high molecular weight, having properties that allow them to be used for the desired purposes, are not currently available.

Now, it was found, surprisingly, that it is possible to create stable L/H-HA cooperative hybrids by submitting aqueous solutions containing H-HA and L-HA together to a suitably configured thermal cycle.

The solutions of stable L/H-HA cooperative hybrids according to the invention are characterized by viscosities that do not change over time and that are notably lower than before the thermal cycle.

Such behaviour cannot be ascribed merely to a process of thermal depolymerization of HA.

There are four parameters that critically determine the formation of the L/H-HA complexes and their rheological properties:
a) the simultaneous presence of the two types of HA (L-HA and H-HA) in the same solution;
b) the molecular weight of the two species of HA used in the process of formation of the L/H-HA hybrid system;
c) the relative proportions of the two species of HA used;
d) the profile of the thermal cycle to which the solution is exposed.

The simultaneous presence of the two types of HA (L-HA and H-HA) in the same solution is a necessary condition because when the solution, submitted to the thermal cycle, reaches a high enough temperature, energy conditions are created that are able simultaneously to rupture all the interactions between the chains of H-HA and those between the chains of L-HA, and in these conditions the prerequisites no longer exist because the weak interactions that develop between the molecules in solution are of the cooperative type and the polymer chains behave as independent entities. Next, when the solution is cooled within the scope of the thermal treatment cycle, interchain interactions begin to reform increasingly, which in this case develop randomly between all the molecules of HA present in solution, both of high and of low molecular weight, giving rise to hybrid systems, which are stabilized when, with increasing number of weak intermolecular bonds, their cooperativeness means that the mode of interaction that has developed between the polymer chains of different molecular weight does not change over time. Confirmation of the validity of this mechanism is the fact that, on submitting two solutions, one of L-HA and one of H-HA, separately to the thermal cycle and then mixing them together after cooling, at equal concentration of the species in solution, we do not observe the dramatic and immediate decrease in viscosity attributed to formation of the hybrid system, which can only form if the two molecular species are present simultaneously during the thermal cycle.

The molecular weight of HA used in constructing L/H-HA hybrid systems critically determines their rheological characteristics; the greater the difference in molecular weight between the L-HA and H-HA used, the greater, at equal concentration, is the decrease in viscosity of the hybrid system relative to that of the H-HA.

Cooperative hybrid L/H-HA complexes, characterized by a decrease in viscosity, can be obtained if the molecular weight of the L-HA is between $1 \cdot 10^4$ and $1 \cdot 10^6$ Da and that of the H-HA is given by the formula $MW_{H-HA} \geq MW_{L-HA}/0.9$.

The relative proportions of L-HA and H-HA, determining the stoichiometry of the hybrid, contribute to modification of their rheological properties relative to the species hybridized between them; the decrease in viscosity due to formation of the complex increases with increase of the L-HA/H-HA stoichiometric ratio used. Normally said ratio is between 0.1 and 10, preferably from 0.5 to 2.

The complexes according to the invention normally have a viscosity from 1.1 to 200-fold less than that of a solution containing the H-HA hyaluronic acid alone used for forming the complex The thermal profile that leads to the formation of cooperative hybrid L/H-HA systems starting from solutions containing L-HA and H-HA envisages that the solution is first heated to temperatures between 80 and 160° C., preferably between 100 and 120° C. and then cooled rapidly to room temperature. The L/H-HA hybrid systems thus obtained are stable over time, attesting to maintenance of their rheological characteristics.

As already mentioned, the solutions of L/H-HA hybrid complexes according to the present invention can easily be obtained by mixing aqueous solutions of H-HA and L-HA of desired molecular weight and submitting the resultant solution to the thermal cycle indicated above; preferably the concentration of the solution of L-HA is between 0.01 and 50% w/w while that of the solution of H-HA is between 0.01 and 10% w/w.

Cooperative hybrid L/H-HA complexes in the solid state can be obtained from solutions containing them in various ways:
a) by precipitation of the solutions containing them, by adding water-miscible organic solvents, such as low molecular weight alcohols, acetone, etc.;
b) by solvent evaporation;
c) by spray-drying;
d) by lyophilization.

Cooperative hybrid complexes similar to those described above, characterized by low values of dynamic viscosity, can moreover be obtained by high-temperature thermal treatment of aqueous solutions of H-HA with low molecular weight polysaccharides, such as chondroitin, chondroitin sulphate, dextrins, cyclodextrins, dextrans.

The cooperative hybrid L/H-HA complexes are, because of their rheological characteristics, of considerable interest in some biomedical applications, for example: biorevitalization of the skin by intradermal injections of HA; techniques of viscosupplementation for resolving pathological situations connected with inflammatory disorders of the joints; intra-bladder treatment of cystitis; treatment of vaginal inflammatory diseases; treatment of alveolar diseases; treatment of oral diseases.

The most important advantage connected with the use of cooperative hybrid L/H-HA complexes is their low viscosity, which in medical practice allows the use of solutions of higher concentration, but still sufficiently fluid to be injected with small-bore needles and catheters or to be nebulized.

Once in contact with the biological environment, the cooperative hybrid L/H-HA complexes behave as systems for slow release of L-HA and H-HA, because the chemical complexity of the microenvironment, characterized by the presence of other species in solution and the enormous surfaces of the cellular structures, permit gradual resolution of the intermolecular interactions that characterize the complex, making both L-HA and H-HA available in context ab initio, molecular species that in vivo have differentiated roles, L-HA that of signalling by interaction with receptors present on the cell surfaces and H-HA as a fundamental constituent of the extracellular matrix.

Non-limiting examples are given below, describing the production, characteristics and use of the cooperative hybrid L/H-HA complexes.

Example 1—Production of Cooperative Hybrid L/H-HA Complexes at Different Temperatures Two aqueous solutions of H-HA (MW $1.4 \cdot 10^6$ Da; Mw/Mn 1.5) and L-HA (MW $3.3 \cdot 10^4$ Da; Mw/Mn 1.8) were prepared at 2% w/v in distilled water, which are used for preparing the various solutions given in Table 1.

These solutions, containing L-HA and H-HA simultaneously, are submitted to a thermal cycle in autoclave that envisages: a) a heating phase from 25° C. up to a maximum temperature in 10 min; b) maintaining this temperature for a specified period of time (10 min or 40 min); c) cooling the solution to 25° C. in 10 min.

MW and polydispersity index Mw/Mn are determined using a size-exclusion chromatography system equipped with a multidetector, consisting of a four-bridge viscosimeter, a refractometer, a right angle light scattering detector (RALS) and a low angle light scattering detector (LALS), patented by the American group Viscotek (www.viscotek.com). The signal measured with the LALS is proportional to the molecular weight and the concentration, that measured with the viscosimetric detector is proportional to the sample concentration and the intrinsic viscosity, while the refractometer provides measurement of the concentration. The Viscotek apparatus not only makes it possible to determine the molecular weight of HA, but also evaluate the degree of non-uniformity of molecular weight in the population of molecules present, described by the polydispersity index Mw/Mn, automatically calculated by the Viscotek apparatus, and defined as the ratio of the average molecular weight (Mw=$\Sigma_i$ $m_i M_i$/$\Sigma_i$ $m_i$ where $m_i$ is the mass of polymer with molecular weight $M_i$ and $\Sigma_i m_i$ is the total mass of polymer, an expression which, setting $m_i$=$n_i M_i$ can also be given as Mw=$\Sigma_i$ $n_i M_i^2$/$\Sigma_i$ $n_i$ $M_i$) and weight-average molecular weight (Mn=$\Sigma_i$ $n_i M_i$/$\Sigma_i$ $n_i$ where $n_i M_i$ is the mass of polymer with molecular weight $M_i$ and $\Sigma_i$ $n_i$ is the total number of moles of polymer present). The measurements of dynamic viscosity $\eta$ are performed on an Anton Paar Physica MCR 301 rheometer, using a geometry with coaxial cylinders. $\eta$ is determined at 25° C. at a constant shear rate ($\gamma'$=$2s^{-1}$) which comes within the range of Newtonian viscosity of the polymer solution ($\eta$ is constant with respect to $\gamma'$ and depends only on the conformation of the polymer in solution).

and L-HA simultaneously leads to quantitative rupture of the hydrogen bonds, causing loss of the conditions of cooperativeness previously existing between the long chains and between the short chains; e) in the subsequent cooling phase, if both short and long chains are present in solution, cooperative interactions with hydrogen bridges can be randomly restored between short and long chains, giving rise to hybrid systems stabilized by cooperative interactions; f) separate heating of solutions of H-HA and L-HA and their subsequent mixing after the cooling phase does not give rise to formation of cooperative hybrids, but to behaviour similar to that described at letter c); g) the L/H-HA hybrid, in the absence of interactions with other molecules or surfaces, remains stable at room temperature because, even if the hydrogen bonds are opened randomly, the presence of a multiplicity of such interactions along the chains keeps the structural elements responsible for bonding at a suitable distance for its reformation; h) the higher the temperature to which the H-HA+L-HA mixture is submitted or the longer the exposure time, the more effective is the formation of the cooperative hybrid.

TABLE 1

| Sample° | Sol. 2% w/v (mL) H-HA | Sol. 2% w/v (mL) L-HA | H₂O (mL) | Initial solution | Mixing with thermal cycle- $T_{max}$ (° C.)-time (min) 120°; 10' | 110°; 10' | 100°; 10' | 100°; 40' |
|---|---|---|---|---|---|---|---|---|
| | | | | | $\eta$ (Pa · s) | | | |
| H-HA | 100 | 0 | 100 | 21.321 | 5.632 | 10.241 | 11.513 | 5.442 |
| L-HA | 0 | 100 | 100 | 0.002 | <0.001 | <0.001 | <0.001 | <0.001 |
| L/H-HA | 100 | 100 | 0 | 19.010 | 0.038 | 0.062 | 0.943 | 0.051 |
| H-HA + L-HA* | 100 | 100 | 0 | — | 4.334 | 9.523 | 10.530 | 4.912 |

*the two solutions at 2% w/v are first treated at high temperature and then mixed in 1:1 ratio by volume.

Table 1—Measurement of the dynamic viscosity of solutions with a concentration of 1% w/v of L-HA (MW $3.3 \cdot 10^4$ Da; Mw/Mn 1.8) and H-HA (MW $1.4 \cdot 10^6$ Da; Mw/Mn 1.5) and of the corresponding stable cooperative L/H-HA complexes with a concentration of 1% w/v and L-HA/H-HA ratio of 1:1 w/w. The thermal treatment cycle in autoclave envisages a heating phase in 10 min from 25° C. to $T_{max}$, remaining at $T_{max}$ for a specified time and a cooling phase from $T_{max}$ to 25° C. in 10 min. The measurements of $\eta$ are taken immediately after the thermal treatment. The data in Table 1 demonstrate that: a) heating of solutions of H-HA in the stated conditions causes a slight hydrolysis of the long polymer chains (120° C., 10 min MW $9.51 \cdot 10^5$ Da; 110° C., 10 min MW $1.04 \cdot 10^6$ Da; 100° C., 10 min MW $1.20 \cdot 10^6$ Da; 100° C., 40 min MW $9.10 \cdot 10^5$ Da) with proportional decrease of $\eta$; b) heating of solutions of L-HA in the stated conditions causes a slight hydrolysis of the polymer chains (120° C., 10 min MW $2.96 \cdot 10^4$ Da; 110° C., 10 min MW $3.12 \cdot 10^4$ Da; 100° C., 10 min MW $3.25 \cdot 10^4$ Da; 100° C., 40 min MW $2.88 \cdot 10^4$ Da) with proportional decrease of $\eta$, which after heating is no longer measurable; c) simple mixing in solution of L-HA and H-HA leads, immediately after mixing, to a slight reduction of $\eta$, because with L-HA of very low molecular weight ($3.3 \cdot 10^4$ Da) there is commencement of activation, even at room temperature, of partial interactions based on hydrogen bonds between short and long chains; d) heating of a solution that contains H-HA Example 2—Production of Cooperative Hybrid L/H-HA Complexes with Different Composition Cooperative hybrid L/H-HA complexes of different composition are prepared by dissolving H-HA (MW $1.4 \cdot 10^6$ Da; Mw/Mn 1.5) and L-HA (MW $3.3 \cdot 10^4$ Da; Mw/Mn 1.8) in 100 mL of water, as shown in Table 2. The resultant solutions are submitted to the following thermal cycle in autoclave: from 25° C. to 120° C. in 10 min, for 10 min at 120° C., from 120° C. to 25° C. in 10 min. The dynamic viscosity of the samples, the MW and the polydispersity index Mw/Mn of L-HA, H-HA and L/H-HA are determined as described in example 1. The data in Table 2 demonstrate the dependence of the viscosity of L/H-HA cooperative complexes on the L-HA/H-HA ratio: the higher the ratio, the lower the viscosity.

TABLE 2

| Sample of L/H-HA (L-HA/H-HA w/w) | L-HA (g in 100 mL of water) | H-HA | Treatment 120° C. - 10 min $\eta$* (Pa · s) | $\eta_{H-HA}$/ $\eta_{L/H-HA}$ |
|---|---|---|---|---|
| 0.0 | 0.0 | 1.0 | 5.632 | — |
| 0.5 | 0.5 | 1.0 | 0.068 | 82.8 |
| 1.0 | 1.0 | 1.0 | 0.038 | 148.2 |
| 1.5 | 1.5 | 1.0 | 0.033 | 170.7 |

*The measurements of $\eta$ are taken immediately after mixing.

Table 2—Measurement of the dynamic viscosity $\eta$ of cooperative hybrid L/H-HA complexes with different L-HA/

H-HA ratio. The concentration of H-HA (MW $1.4 \cdot 10^6$ Da; Mw/Mn 1.5) is kept constant at 1% w/v, while that of L-HA (MW $3.3 \cdot 10^4$ Da; Mw/Mn 1.8) varies from 0 to 1.5% w/v. The thermal treatment cycle in autoclave envisages a heating phase of 10 min from 25° C. to $T_{max}$, remaining at $T_{max}$ for a specified time and a cooling phase from $T_{max}$ to 25° C. in 10 min. The measurements of η are taken immediately after the thermal treatment.

Example 3—Production of Cooperative Hybrid L/H-HA Complexes Using L-HA of Different Molecular Weight Aqueous solutions of H-HA (MW $1.4 \cdot 10^6$ Da; Mw/Mn 1.5), L-HA (MW $3.3 \cdot 10^4$ Da; Mw/Mn 1.8) and L-HA (MW $2.2 \cdot 10^5$ Da; Mw/Mn 1.7) are prepared at 2% w/v in distilled water, which are used for preparing the various solutions given in Table 3. The resultant solutions are submitted to the following thermal cycle in autoclave: from 25 to 120° C. in 10 min, for 10 min at 120° C., from 120 to 25° C. in 10 min. The dynamic viscosity η of the samples, the MW and the polydispersity index Mw/Mn of L-HA, H-HA and L/H-HA are determined as described in example 1.

The data in Table 3 demonstrate that, all other parameters being equal, the lower the MW of L-HA in the cooperative hybrid, the greater is the decrease of η. On comparing the values of η of L/H-HA hybrid complexes using L-HA with MW $3.3 \cdot 10^4$ Da or $2.20 \cdot 10^6$ Da the value of the ratio $\eta_{H-HA}/\eta_{L/H-HA}$ increases about 50-fold.

TABLE 3

| Sample | Sol. 2% p/v (mL) | | H$_2$O (mL) | Thermal treatment 120°; 10 min η (Pa · s) | $\eta_{H-HA}/\eta_{L/H-HA}$ |
|---|---|---|---|---|---|
| | H-HA | L-HA | | | |
| H-HA | 100 | 0 | 100 | 5.632 | — |
| L-HA $3.3 \cdot 10^4$ Da | 0 | 100 | 100 | <0.001 | — |
| L-HA $2.2 \cdot 10^5$ Da | 0 | 100 | 100 | 0.016 | — |
| L/H-HA $3.3 \cdot 10^4$ Da | 100 | 100 | 0 | 0.038 | 148.2 |
| L/H-HA $2.2 \cdot 10^5$ Da | 100 | 100 | 0 | 1.771 | 3.0 |

Table 3—Measurement of the dynamic viscosity η of cooperative hybrid L/H-HA complexes with L-HA/H-HA ratio of 1 w/w, constructed with L-HA of different MW. Aqueous solutions of H-HA (MW $1.4 \cdot 10^6$ Da; Mw/Mn 1.5), L-HA (MW $3.3 \cdot 10^4$ Da; Mw/Mn 1.8) and L-HA (MW $2.2 \cdot 10^5$ Da; Mw/Mn 1.7) are prepared at 2% w/v in distilled water, which are used for preparing the various solutions given in the table. The resultant solutions are submitted to the following thermal cycle in autoclave: from 25 to 120° C. in 10 min, for 10 min at 120° C., from 120 to 25° C. in 10 min.

Example 4—Kinetic Analysis of Formation of Cooperative Hybrid L/H-HA Complexes with and without Thermal Cycle Aqueous solutions of H-HA (MW $1.4 \cdot 10^6$ Da; Mw/Mn 1.5), L-HA (MW $3.3 \cdot 10^4$ Da; Mw/Mn 1.8) and L-HA (MW $2.2 \cdot 10^5$ Da; Mw/Mn 1.7) are prepared at 2% w/v in distilled water, which are used for preparing the various solutions given in Table 4. Half of the resultant solutions are maintained at temperature and the other half are first submitted to the following thermal cycle in autoclave: from 25 to 120° C. in 10 min, for 10 min at 120° C., from 120 to 25° C. in 10 min and are then maintained at room temperature. The dynamic viscosity η is measured over time, for both series of samples. The MW, the polydispersity index Mw/Mn of L-HA, H-HA and L/H-HA and the dynamic viscosity η of the samples are determined as described in example 1.

The data in Table 4 demonstrate that: a) when MW of L-HA is of the order of $10^4$ Da, formation of L/H-HA cooperative complexes begins, even if slowly, even at room temperature, because the lower cooperativeness that exists between the short chains of L-HA allows these to compete in the cooperative interactions existing between the long chains of H-HA, giving rise to the formation of hybrid systems; b) for this reason the solutions obtained by mixing, at room temperature, H-HA and L-HA with MW of the order of $10^4$ Da, display a dynamic viscosity that varies over time; c) conversely, the thermal treatment generates, in a few minutes, cooperative hybrid complexes, which once they reach a condition of equilibrium do not display a change in their dynamic viscosity over time; d) when the MW of L-HA is of the order of $10^5$, in the absence of thermal treatment, simple mixing of the two solutions does not significantly alter their dynamic viscosity over time, owing to the strong cooperativeness preexisting between the chains of L-HA, which prevents their interaction with the chains of H-HA.

TABLE 4

| | 120°; 10' | | Without thermal treatment Time (days) | | | |
|---|---|---|---|---|---|---|
| | 0 | 10 | 0 | 4 | 14 | 24 |
| Sample | η (Pa · s) | | | | | |
| H-HA + L-HA $3.3 \cdot 10^4$ Da | 0.04 | 0.04 | 19.01 | 6.91 | 1.05 | 0.68 |
| H-HA + L-HA $2.20 \cdot 10^5$ Da | 1.77 | 1.77 | 24.03 | 23.71 | 22.41 | 21.01 |

Table 4—Kinetics of the dynamic viscosity η of cooperative hybrid L/H-HA complexes with L-HA/H-HA ratio of 1 w/w, constructed with L-HA of different MW. Aqueous solutions of H-HA (MW $1.4 \cdot 10^6$ Da; Mw/Mn 1.5), L-HA (MW $3.3 \cdot 10^4$ Da; Mw/Mn 1.8) and L-HA (MW $2.2 \cdot 10^5$ Da; Mw/Mn 1.7) are prepared at 2% w/v in distilled water, which are used for preparing the various solutions given in the table. Half of the resultant solutions are maintained at temperature and half are first submitted to the following thermal cycle in autoclave: from 25 to 120° C. in 10 min, for 10 min at 120° C., from 120 to 25° C. in 10 min and are then maintained at room temperature.

Example 5—Preparation of Cooperative Hybrid L/H-HA Complexes in the Solid State by Precipitation from Solution Containing Them The aqueous solution of the cooperative hybrid L/H-HA complex, obtained as described in example 1 with a thermal cycle that envisages exposure to a $T_{max}$ of 120° C. for 10 min, is treated with 2 volumes of anhydrous ethanol, added slowly and with stirring. A white pulverulent precipitate is obtained, which sediments rapidly and can be dried under vacuum with heating. The process leads to formation of a white dry powder, at a yield of 99% relative to the theoretical value. The cooperative hybrid L/H-HA complex in powder, if dissolved in water at a concentration of 1% w/w, gives a solution that has the same value of dynamic viscosity η as the solution precipitated initially.

Example 6—Preparation of Cooperative Hybrid L/H-HA Complexes in the Solid State by Lyophilization of Solutions Containing Them The aqueous solution of the cooperative hybrid L/H-HA complex, obtained as described in example 1 with a thermal cycle that envisages exposure to a $T_{max}$ of 120° C. for 10 min is lyophilized. A spongy mass is obtained, which is easily transformed into a white powder by mechanical treatment. The yield of lyophilized powder coincides with the theoretical value. The cooperative hybrid L/H-HA complex lyophilized in powder, if dissolved in water at a concentration 1% w/w, gives a solution that has the same value of dynamic viscosity η as the solution precipitated initially.

Example 7—Preparation of Cooperative Hybrid C/H-HA and CS/H-HA Complexes

Aqueous solutions of H-HA (MW 1.4·10$^6$ Da; Mw/Mn 1.5), chondroitin (C; MW 6.6·10$^4$ Da; Mw/Mn 1.4) and chondroitin sulphate (CS; MW 3.8·10$^4$ Da; Mw/Mn 1.4) are prepared at 2% w/v in distilled water, which are used for preparing the various solutions given in Table 5. The resultant solutions are submitted to the following thermal cycle in autoclave: from 25 to 120° C. in 10 min, for 10 min at 120° C., from 120 to 25° C. in 10 min. The dynamic viscosity η of the samples, the MW and the polydispersity index Mw/Mn of L-HA, H-HA and L/H-HA are determined as described in example 1.

The data in Table 5 demonstrate that: a) both chondroitin and chondroitin sulphate, with MW of the order of magnitude of 10$^4$ Da, give rise by thermal treatment to the formation of stable cooperative hybrid C/H-HA and CS/H-HA complexes, characterized by a low value of dynamic viscosity η; b) simple mixing of solutions of C and CS with that of H-HA does not produce significant changes in dynamic viscosity η; c) the $\eta_{pre}/\eta_{post}$ ratio of the C/H-HA complex is about double that of the CS/H-HA complex.

TABLE 5

| Sample | Sol. 2% p/v (mL) H-HA | Sol. 2% p/v (mL) L-HA | H$_2$O (mL) | Thermal pretreatment η (Pa·s) | Thermal post-treatment 120°; 10 min η (Pa·s) | $\eta_{pre}/\eta_{post}$ |
|---|---|---|---|---|---|---|
| H-HA | 100 | 0 | 100 | 21.321 | 5.632 | — |
| C | 0 | 100 | 100 | 0.004 | 0.002 | — |
| CS | 0 | 100 | 100 | 0.002 | 0.001 | — |
| C/H-HA | 100 | 100 | 0 | 22.832 | 0.873 | 27.3 |
| CS/H-HA | 100 | 100 | 0 | 22.915 | 1.728 | 13.2 |

Table 5—Measurement of the dynamic viscosity η of cooperative hybrid C/H-HA and CS/H-HA complexes. Aqueous solutions of H-HA (MW 1.4·10$^6$ Da; Mw/Mn 1.5), C (MW 6.6·10$^4$ Da; Mw/Mn 1.4) and CS (MW 3.8·10$^4$ Da; Mw/Mn 1.4) are prepared at 2% w/v in distilled water, which are used for preparing the various solutions given in the table. The resultant solutions are submitted to the following thermal cycle in autoclave: from 25 to 120° C. in 10 min, for 10 min at 120° C., from 120 to 25° C. in 10 min.

Example 8—Use of Cooperative Hybrid L/H-HA Complexes in the Field of Biorevitalization 4 g of the cooperative hybrid complex obtained as described in example 1 is dissolved in 100 mL of saline, heating at 120° C. for 10 min, and then drying the complex by lyophilization, as described in example 5. The hyaluronic acid used is of pharmaceutical grade for injection and all the manipulations are carried out in conditions that guarantee sterility and apyrogenicity of the solution. The solution containing 40 mg/mL of L/H-HA complexes is introduced into 1 mL syringes fitted with a gauge 30 needle. The treatment of biorevitalization of the face is conducted on 10 informed volunteers, who have obvious signs of cutaneous ageing of the face. The experimental design envisages that each subject undergoes an identical treatment of biorevitalization by subcutaneous microinjection on the right side of the face with the formulation of the invention (1 mL) and on the left side with a primary product already marketed (1 mL). The results obtained, objectivized instrumentally, demonstrate the superiority of the treatment with the stable cooperative L/H-HA complex, both in terms of quality and duration of the treatment.

Example 9—Use of Cooperative Hybrid L/H-HA Complexes in the Field of Viscosupplementation 4 g of the cooperative hybrid complex obtained as described in example 1 is dissolved in 100 mL of saline, heating at 120° C. for 10 min, and then drying the complex by lyophilization, as described in example 5. The hyaluronic acid used is of pharmaceutical grade for injection and all the manipulations are carried out in conditions that guarantee sterility and apyrogenicity of the solution. The solution containing 40 mg/mL of L/H-HA complexes is introduced into 1 mL syringes fitted with a gauge 30 needle. The viscosupplementation treatment is conducted on 5 informed volunteers, with a bilateral knee disorder, the therapeutic indication being infiltration of hyaluronic acid in the joint. The experimental design envisages that each subject receives identical treatment of viscosupplementation in the right joint with the formulation of the invention (1 mL) and in the left joint with a primary product already marketed (1 mL). The results obtained, objectivized instrumentally, demonstrate the superiority of the treatment with the stable cooperative L/H-HA complex, both in terms of rapid reduction of pain and efficacy of resolution of the pathological condition.

The invention claimed is:

1. A method of preparing a, hybrid L/H-HA complex with the method comprising:
    mixing L-HA hyaluronic acid or hyaluronans and H-HA hyaluronic acid or hyaluronans in a solvent to obtain a solution;
    submitting to a thermal treatment comprising maintaining at a temperature of about 100° for 40 minutes, said solution containing simultaneously said L-HA hyaluronic acid or hyaluronans and said H-HA hyaluronic acid or hyaluronans, wherein the molecular weight of L-HA is comprised between $1\times10^4$ to $1\times10^6$ Da and that of H-HA is $1.4\times10^6$ Da.

2. The method according to claim 1, wherein L-HA/H-HA ratio is between 0.1 and 10.

3. The method according to claim 1 wherein said L/H-HA complexes have a viscosity less than a solution containing H-HA hyaluronic acid alone.

4. The method according to claim 3, wherein other chemical species in addition to solvent and hyaluronic acid are also present in the solution.

5. The method according to claim 1, wherein the solvent used is water.

6. The method according to claim 1, wherein the thermal treatment is carried out in autoclave.

7. The method according to claim 1, wherein said L/H-HA complexes are prepared in the solid state by precipitation of the solutions containing them.

8. Method according to claim 7, wherein the precipitation is obtained by adding a compound miscible with the solution and acting as a non-solvent for the complex.

9. Method according to claim 8, wherein the non-solvent compound for the complex is a water-miscible organic solvent, selected from the group consisting of acetone, methanol, ethanol, propanol, isopropanol and butanol.

10. Method according to claim 1, wherein said L/H-HA complexes are prepared by removing the solvent by means of vacuum evaporation, spray-drying or freeze-drying in the dry state.

11. A method of preparing a hybrid of low molecular weight polysaccharides/H-HA complex with the method comprising:

mixing low molecular weight polysaccharides having molecular weight of $1\times10^4$ to $1\times10^6$ Da and H-HA hyaluronic acid or hyaluronans in a solvent to obtain a solution;

submitting to a thermal treatment comprising maintaining at a temperature of about 100° for 40 minutes, said solution containing simultaneously said low molecular weight polysaccharides and said H-HA hyaluronic acid or hyaluronans wherein the low molecular weight polysaccharides are selected from the group consisting of chondroitin, chondroitin sulphate, dextrins, cyclodextrins, dextrans and the molecular weight of the H-HA is given by the formula MWH-HA$\geq$low molecular weight polysaccharides/0.9.

12. Method according to claim 11 wherein by low molecular weight of polysaccharides is meant less than one million of Da.

\* \* \* \* \*